(12) United States Patent
Kuwagaki et al.

(10) Patent No.: US 12,065,548 B2
(45) Date of Patent: Aug. 20, 2024

(54) GENERALLY SPHERICAL RESIN PARTICLES FORMED OF THERMOPLASTIC RESIN, METHOD FOR PRODUCING SAME AND USE OF SAME

(71) Applicant: SEKISUI PLASTICS CO., LTD., Osaka (JP)

(72) Inventors: Kaori Kuwagaki, Nara (JP); Akiyoshi Kusaka, Nara (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 100 days.

(21) Appl. No.: 17/347,864

(22) Filed: Jun. 15, 2021

(65) Prior Publication Data

US 2021/0309811 A1   Oct. 7, 2021

Related U.S. Application Data

(63) Continuation of application No. 16/318,808, filed as application No. PCT/JP2016/071636 on Jul. 22, 2016, now Pat. No. 11,078,338.

(51) Int. Cl.

| | | |
|---|---|---|
| *C08J 3/16* | (2006.01) | |
| *A61K 8/02* | (2006.01) | |
| *A61K 8/85* | (2006.01) | |
| *A61Q 19/00* | (2006.01) | |
| *C08G 63/06* | (2006.01) | |
| *C08G 63/08* | (2006.01) | |
| *C08G 63/16* | (2006.01) | |
| *C08J 3/11* | (2006.01) | |
| *C08J 3/12* | (2006.01) | |
| *C09D 5/03* | (2006.01) | |
| *C09D 167/02* | (2006.01) | |
| *C09D 167/04* | (2006.01) | |

(52) U.S. Cl.
CPC ............. *C08J 3/16* (2013.01); *A61K 8/025* (2013.01); *A61K 8/85* (2013.01); *A61Q 19/00* (2013.01); *C08G 63/06* (2013.01); *C08G 63/08* (2013.01); *C08G 63/16* (2013.01); *C08J 3/11* (2013.01); *C08J 3/12* (2013.01); *C09D 5/031* (2013.01); *C09D 167/02* (2013.01); *C09D 167/04* (2013.01); *A61K 2800/26* (2013.01); *C08G 2230/00* (2013.01); *C08J 2367/02* (2013.01); *C08J 2367/04* (2013.01)

(58) Field of Classification Search
CPC ......... C08J 3/16; C08J 3/11; C08J 3/12; C08J 2367/02; C08J 2367/04; C08J 3/14; C08J 2300/16; C08J 3/095; C08J 2367/00; C08J 2371/00; A61K 8/025; A61K 8/85; A61K 2800/26; A61K 2800/10; A61K 2800/412; A61K 8/922; A61Q 19/00; C08G 63/06; C08G 63/08; C08G 63/16; C08G 2230/00; C08G 63/88; C09D 5/031; C09D 167/02; C09D 167/04
See application file for complete search history.

(56) References Cited

U.S. PATENT DOCUMENTS

| | | | |
|---|---|---|---|
| 6,127,513 | A | 10/2000 | Ohara et al. |
| 6,190,773 | B1 | 2/2001 | Imamura et al. |
| 2012/0258310 | A1 | 10/2012 | Watanabe et al. |
| 2013/0183528 | A1 | 7/2013 | Echigo et al. |
| 2013/0309497 | A1 | 11/2013 | Takezaki et al. |
| 2014/0024748 | A1 | 1/2014 | Hans et al. |
| 2014/0026916 | A1 | 1/2014 | Havens et al. |
| 2015/0030842 | A1 | 1/2015 | Hama et al. |
| 2016/0311995 | A1 | 10/2016 | Otsubo et al. |
| 2018/0105669 | A1 | 4/2018 | Otsubo et al. |

FOREIGN PATENT DOCUMENTS

| | | |
|---|---|---|
| CN | 103834054 | 6/2014 |
| JP | 5-194141 | 8/1993 |
| JP | 9-59358 | 3/1997 |
| JP | 10-316750 | 12/1998 |
| JP | 11-35693 | 2/1999 |
| JP | 2000-7789 | 1/2000 |
| JP | 2001-288273 | 10/2001 |
| JP | 2002-187810 | 7/2002 |
| JP | 2002-265333 | 9/2002 |
| JP | 2002-356558 | 12/2002 |
| JP | 2004-43557 | 2/2004 |
| JP | 2004-231760 | 8/2004 |
| JP | 2004-269865 | 9/2004 |
| JP | 2004-345980 | 12/2004 |
| JP | 2005-2302 | 1/2005 |
| JP | 2005-200663 | 7/2005 |
| JP | 2006-321711 | 11/2006 |
| JP | 2007-119632 | 5/2007 |
| JP | 2007-219183 | 8/2007 |
| JP | 2008-7668 | 1/2008 |
| JP | 2009-242728 | 10/2009 |
| JP | 2010-241785 | 10/2010 |
| JP | 2011-105673 | 6/2011 |
| JP | 2012-211111 | 11/2012 |

(Continued)

OTHER PUBLICATIONS

Mitsubishi Chemical BioPBS Catalog, p. 1.

(Continued)

*Primary Examiner* — Robert S Cabral

(74) *Attorney, Agent, or Firm* — Wenderoth, Lind & Ponack, L.L.P.

(57) ABSTRACT

Generally spherical resin particles formed of a thermoplastic resin, having a sphericity of 0.90 to 1.00, a light scattering index of 0.5 to 1.0 and a linseed oil absorption of 30 to 150 mL/100 g.

11 Claims, 1 Drawing Sheet

(56) References Cited

FOREIGN PATENT DOCUMENTS

| JP | 2013-133473 | 7/2013 |
|---|---|---|
| JP | 2014-505769 | 3/2014 |
| KR | 2003-0067867 | 8/2003 |
| KR | 10-2016-0080527 | 7/2016 |
| WO | 2006/126563 | 11/2006 |
| WO | 2011/093488 | 8/2011 |
| WO | 2012/105140 | 8/2012 |
| WO | 2013/046860 | 4/2013 |
| WO | 2015/098654 | 7/2015 |
| WO | 2016/104140 | 6/2016 |

OTHER PUBLICATIONS

Pepić, Dragana et al., "Dobijanje Poroznih Biodegradabilnih Mikrosfera Poli(Butilen Sukcinata)/Preparation of Biodegradable Porous Poly(Butylene Succinate) Microspheres," Hemijska Industrija. 2008, vol. 62, No. 6, pp. 329-338, with English language summary (last page).
International Search Report dated Sep. 13, 2016 in International Application No. PCT/JP2016/071636.
Supplementary European Search Report dated Feb. 28, 2020 in corresponding European Patent Application No. 16909555.1.
Database WPI, Week 201639 (Jun. 2, 2016), Thomson Scientific, London, GB; AN 2016-324559, XP002797617.
Database WPI, Week 201603 (Dec. 3, 2015), Thomson Scientific, London, GB; AN 2015-75111D, XP002797618.
Extended European Search Report issued Aug. 2, 2023, in European Application No. 23162564.1.
Database WPI, Week 201450 (Jun. 4, 2014), Thomson Scientific, London, GB; AN 2014-P25144, XP002809791, which corresponds to Ref. BA and is cited by CA.
Database WPI, Week 201348 (Jul. 8, 2013), Thomson Scientific, London, GB; AN 2013-L68405, XP002809792, which corresponds to Ref. BB and is cited by CA.
Database WPI, Week 200708 (Nov. 30, 2006), Thomson Scientific, London, GB; AN 2007-083526, XP002809793, which corresponds to Ref. BC and is cited by CA.

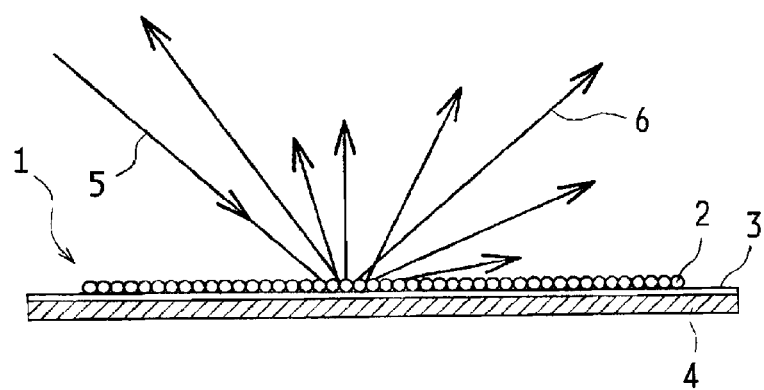

GENERALLY SPHERICAL RESIN PARTICLES FORMED OF THERMOPLASTIC RESIN, METHOD FOR PRODUCING SAME AND USE OF SAME

TECHNICAL FIELD

The present invention related to generally spherical resin particles formed of a thermoplastic resin having high sphericity and excellent optical properties and handling characteristics at the time of compounding, a method for producing the same and use of the same.

BACKGROUND ART

Thermoplastic resin particles have a large specific surface area and advantageous particle structures, and thus are used for modification and improvement of various materials. Main applications include compounding agents for cosmetics such as foundations, antiperspirants and scrubes, various agents including flatting agents for paints, rheology modifying agents, antiblocking agents, lubricity imparting agents, light diffusing agents and medical diagnostic examination agents, additives for molded articles including automobile materials and construction materials.

Meanwhile, with recent increasing interest in environmental issues, it is required to use materials derived from nonpetroleum raw materials in all fields where resins are used in order to reduce the effects on the environment. For example, there are similar requirements in the fields where resin particles are used such as cosmetics and paints.

Known methods for producing thermoplastic resin particles include the crushing method typically including freeze crushing (Japanese Unexamined Patent Application Publication No. 2001-288273: Patent Document 1); the solvent dissolution/deposition method in which a resin is dissolved in a solvent at high temperature and then cooled to deposit the resin or a resin is dissolved in a solvent to which a poor solvent is then added to deposit the resin (Japanese Unexamined Patent Application Publication No. 2000-7789: Patent Document 2, Japanese Unexamined Patent Application Publication No. 2005-2302: Patent Document 3, Japanese Unexamined Patent Application Publication No. 2009-242728: Patent Document 4, Japanese Unexamined Patent Application Publication No. H11-35693: Patent Document 5); the melt-kneading method in which a thermoplastic resin and an incompatible resin are mixed in a mixer such as a biaxial extruder to form a resin composition containing the thermoplastic resin in the dispersed phase and the resin incompatible with the thermoplastic resin in the continuous phase, followed by removal of the incompatible resin to obtain thermoplastic resin particles (Japanese Unexamined Patent Application Publication No. 2004-269865: Patent Document 6, Japanese Unexamined Patent Application Publication No. 2005-200663: Patent Document 7) and the like.

Particularly, in order to obtain particles formed of biodegradable resins, Patent Document 1 proposes obtaining fine particles by mechanically crushing and classifying chips or mass of a polylactic acid-based resin while cooling to a low temperature of −50° C. to −180° C. without using organic solvent. Patent Documents 2 to 4 propose dissolving a polylactic acid-based resin in an organic solvent and adding the solution dropwise to a poor solvent such as water or neutralizing or converting to a salt, thereby depositing fine particles.

Patent Document 8 (WO2012/105140) proposes a method for obtaining porous polylactic acid-based resin particles having a small particle diameter and high oil absorption by dissolving polylactic acid and another resin in an ether-based solvent, applying shear force to form an emulsion and bringing the emulsion into contact with a poor solvent.

CITATION LIST

Patent Literatures

Patent Document 1: Japanese Unexamined Patent Application Publication No. 2001-288273
Patent Document 2: Japanese Unexamined Patent Application Publication No. 2000-7789
Patent Document 3: Japanese Unexamined Patent Application Publication No. 2005-2302
Patent Document 4: Japanese Unexamined Patent Application Publication No. 2009-242728
Patent Document 5: Japanese Unexamined Patent Application Publication No. H11-35693
Patent Document 6: Japanese Unexamined Patent Application Publication No. 2004-269865
Patent Document 7: Japanese Unexamined Patent Application Publication No. 2005-200663
Patent Document 8: WO 2012/105140

SUMMARY OF INVENTION

Technical Problems

However, conventional thermoplastic resin particles obtained according to the production methods disclosed in Patent Documents 1 to 7 have such problems that the obtained particles are not spherical, the particle diameter is large, the particle size distribution is wide and fibrous substances are included in some cases. Among others, in the field of cosmetics in which tactile sensation and texture are important and the field of paints in which rheology control is important, conventional thermoplastic resin particles do not sufficiently yield the effect of addition of fine particles.

Particularly, thermoplastic biodegradable resins tend to be too soft or too viscous. Because of this, during production of powder by general mechanical crushing,
(1) it may be difficult to obtain fine powder;
(2) because of fragility thereof, the obtained powder may be a mixture of particles having large diameters and those having minute diameters; and
(3) because of crushing into smaller particles during use, the polishing effect does not last long.

In addition, although the technique disclosed in Patent Document 1 allows production of powder, it is still difficult to produce fine powder. Further, complicated facilities for handling a coolant such as liquid nitrogen may be required and the time required for production is significantly extended due to additional steps, and thus the productivity is significantly reduced.

In Patent Documents 2 to 4, not only the productivity is reduced due to requirements of multiple steps such as dissolution, deposition and drying, but also a high amount of waste solvent containing impurities is generated. Discharge of the waste solvent very possibly has a negative impact on the environment, and it is laborious to remove the impurities in order to recycle the solvent. In addition, it is highly possible that during the treatment, substances that may have a negative impact on the environment may be generated. Further, the obtained powder inevitably contains a minute amount of residual solvent which may affect the quality of the final product.

Particularly in Patent Document 4, a polylactic acid-based resin is dissolved in benzene and then m-xylene is mixed at less than 60° C. to deposit polylactic acid-based resin powder, and thus not only a large amount of organic solvent is required, but also the resin may contain residual organic solvent. Further, even when spherical particles can be obtained, optical properties may not be sufficiently exerted particularly when used in the fields of, for example, cosmetics and paints.

In Patent Document 8, although smooth fine particles can be obtained, the particles do not have sufficiently excellent sphericity and light scattering index.

Solution to Problems

The inventors of the present invention found that the above problems may be solved by defining the sphericity, light scattering properties and linseed oil absorption of resin particles within specific ranges, thereby achieving the present invention. The inventors of the present invention also found that the resin particles can be prepared by using, as a solvent for emulsifying and dispersing thermoplastic resin particles, an alcohol solvent that has high solubility of the resin at high temperature while having low solubility of the resin at normal temperature, has a specific structure and is highly safe.

Accordingly, the present invention provides generally spherical resin particles formed of a thermoplastic resin, having a sphericity of 0.90 to 1.00, a light scattering index of 0.5 to 1.0 and a linseed oil absorption of 30 to 150 mL/100 g.

The present invention also provides a method for producing the generally spherical resin particles formed of a thermoplastic resin, wherein the generally spherical resin particles formed of the thermoplastic resin are obtained by emulsifying and dispersing the thermoplastic resin at a temperature of 100° C. or higher in the presence of a solvent containing 3-alkoxy-3-methyl-1-butanol and/or 3-alkoxy-3-methyl-1-butylacetate (the alkoxy group has 1 to 5 carbon atoms), water and a dispersion stabilizer followed by cooling.

The present invention further provides a cosmetic containing the generally spherical resin particles formed of a thermoplastic resin.

The present invention further provides a coating material containing the generally spherical resin particles formed of a thermoplastic resin.

Advantageous Effects of Invention

The present invention can provide generally spherical thermoplastic resin particles having high light scattering ability. The present invention can also provide a production method that allows convenient preparation of the resin particles.

It is also possible to provide generally spherical thermoplastic resin particles having higher light scattering ability in any of the following cases:
(1) the thermoplastic resin is at least one resin selected from the group consisting of a polyolefin-based resin, a polyester-based resin, a polyether-based resin and a polyamide-based resin;
(2) the thermoplastic resin is at least one resin selected from the group consisting of polyethylene, polypropylene, an ethylene/vinyl acetate copolymer, an ethylene/(meth)acrylic acid copolymer, an ethylene/(meth)acrylate ester copolymer, polylactic acid, polybutylene succinate, polyhydroxyalkanoate, Nylon 12, Nylon 6 and polycaprolactam.
(3) the thermoplastic resin is biodegradable and is at least one resin selected from the group consisting of a polyester-based resin and a polyether-based resin.
(4) the thermoplastic resin is dissolved or plasticized in 3-alkoxy-3-methyl-1-butanol and/or 3-alkoxy-3methyl-1-butylacetate (the alkoxy group has 1 to 5 carbon atoms) at 100° C. or higher and is not dissolved therein at normal temperature.

BRIEF DESCRIPTION OF DRAWINGS

FIG. 1 is a schematic view illustrating the method for measuring the light scattering index.

DESCRIPTION OF EMBODIMENTS (Generally Spherical Resin Particles Formed of a Thermoplastic Resin: Hereinafter Also Referred to as Generally Spherical Particles)

(1) Properties

The generally spherical particles have a sphericity of 0.90 to 1.00, a light scattering index of 0.5 to 1.0 and a linseed oil absorption of 30 to 150 mL/100 g. Methods for measuring the sphericity, light scattering index and linseed oil absorption are described in Examples.

When the sphericity is less than 0.90, cosmetics or the like containing the generally spherical particles may have decreased flowability and deteriorated tactile sensation and lubricity. The sphericity may be 0.90, 0.92, 0.93, 0.95, 0.97 or 1.00. The sphericity is preferably 0.92 to 1.00 and more preferably 0.93 to 1.00.

When the light scattering index is less than 0.5, light scattering ability may be insufficient and cosmetics or the like containing the generally spherical particles may have poor soft focus property. The light scattering index may be 0.5, 0.55, 0.6, 0.65, 0.7, 0.75, 0.8, 0.85, 0.9, 0.95 or 1.0. The light scattering index is preferably 0.55 to 1.0 and more preferably 0.6 to 1.0.

When the linseed oil absorption is within the above range, the generally spherical particles may have preferable handling characteristics at the time of compounding during production of products containing the generally spherical particles. When the linseed oil absorption is less than 30 mL/100 g, cosmetics or the like containing the generally spherical particles may easily cause smeared makeup and makeup may not last long. When the linseed oil absorption is above 150 mL/100 g, the generally spherical particles may absorb other components and have reduced flowability, thereby deteriorating handling characteristics. The linseed oil absorption may be 30 mL/100 g, 50 mL/100 g, 80 mL/100 g, 100 mL/100 g, 120 mL/100 g, 145 mL/100 g or 150 mL/100 g. The linseed oil absorption is more preferably 30 to 145 mL/100 g.

The generally spherical particles preferably has a volume average particle diameter of 1 to 500 μm. The volume average particle diameter may be 1 μm, 3 μm, 10 μm, 20 μm, 50 μm, 100 μm, 200 μm, 300 μm, 400 μm or 500 μm. The generally spherical particles may have various particle diameters according to the application. For example, the particle diameter may be appropriately selected according to the application such as 3 to 20 μm for foundations, 200 to 500 μm for scrubs, and 3 to 100 μm for paints. The measurement method of the average particle diameter is described in Examples.

(2) Thermoplastic Resin

The thermoplastic resin is not particularly limited and examples thereof include at least one resin selected from the group consisting of a polyolefin-based resin, a polyester-based resin, a polyether-based resin and a polyamide-based resin. Examples of the polyolefin-based resin include polyethylene, polypropylene, ethylene/vinyl acetate copolymers, ethylene/(meth)acrylic acid copolymers, ethylene/(meth) acrylate ester copolymers and the like. Examples of the ester component of the (meth)acrylate ester include methyl, ethyl, propyl, butyl and the like. Examples of the polyester-based resin include polylactic acid, polybutylene succinate, polyhydroxyalkanoate, polycaprolactam and the like. A preferred polyhydroxyalkanoate is a poly(3-hydroxyalkanoate)polymer or copolymer having repeating units represented by general formula (1) [—CH(R)—CH$_2$CO—O—] (wherein R is an alkyl group represented by —C$_n$H$_{2n+1}$ and n is an integer of 1 to 15). More specifically, a copolymer of 3-hydroxybutyrate and at least one monomer selected from the group consisting of 3-hydroxypropionate, 3-hydroxyvalerate, 3-hydroxyhexanoate, 3-hydroxyheptanoate, 3-hydroxyoctanoate, 3-hydroxynonanate, 3-hydroxydecanoate, 3-hydroxytetradecanoate, 3-hydroxyhexadecanoate, 3-hydroxyoctadecanoate, 4-hydroxybutyrate, 4-hydroxyvalerate, 5-hydroxyvalerate and 6-hydroxyhexanoate. Specific examples of the (3-hydroxyalkanoate)polymer or copolymer include homopolymers of 3-hydroxyalkanoate, copolymers formed from two or more 3-hydroxyalkanoates having different values for n and blends of two or more selected from the group of the homopolymers and the copolymers. Among others, homopolymers or copolymers containing repeating units selected from the group consisting of 3-hydroxybutyrate repeating units wherein n=1, 3-hydroxyvalerate repeating units wherein n=2, 3-hydroxyhexanoate repeating units wherein n=3, 3-hydroxyoctanoate repeating units wherein n=5 and 3-hydroxyoctadecanoate repeating units wherein n=15 and blends thereof are preferred, and copolymers containing 3-hydroxybutyrate repeating units and at least one type of repeating unit selected from the group consisting of 3-hydroxyvalerate, 3-hydroxyhexanoate and 3-hydroxyoctanoate. Poly(3-hydroxybutyrate-co-3-hydroxyhexanoate), which is a copolymer containing 3-hydroxybutyrate repeating units and 3-hydroxyhexanoate units, is the most preferable. More specific examples include polymers under the product name of Aonilex series manufactured by Kaneka Corporation. Examples of the polyether-based resin include polyethersulfone and the like. Examples of the polyamide-based resin include Nylon 12, Nylon 6 and the like. The exemplified resins may be used respectively alone or as a mixture of more than one resin. The thermoplastic resin may have any molecular weight without limitation. The molecular weight may be appropriately selected according to the final application and purpose.

The production method of the present invention may be applied to at least one resin that is selected from the group consisting of a polyester-based resin and a polyether-based resin and is biodegradable which is generally difficult to be obtained in the form of particles. Examples of such a resin include polyester-based resins such as polylactic acid, polybutylene succinate, polyhydroxyalkanoate, polycaprolactone and the like.

The thermoplastic resin is preferably dissolved or plasticized in specific solvents described in the section of production method hereinafter at a high temperature but does not dissolve at normal temperature (about 25° C.). The resins having such properties can conveniently provide generally spherical particles having specific sphericity and light scattering index.

(3) Additional Components

The generally spherical particles may contain, as needed, well-known flowability controlling agent, ultraviolet absorbing agent, light stabilizer, pigment (such as extender pigment, color pigment, metal pigment and mica powder pigment), dye and the like.

(4) Application

The generally spherical particles may be used for applications including compounding agents for cosmetics such as foundations, antiperspirants and scrubes; various agents including flatting agents for paints, rheology modifying agents, antiblocking agents, lubricity imparting agent, light diffusing agents, auxiliary agents for sinter molding of fine ceramics, fillers for adhesives, medical diagnostic examination agents and the like; additives for molded articles such as automobile materials and construction materials and the like.

(Production Method of Generally Spherical Resin Particles Formed of a Thermoplastic Resin)

The generally spherical particles may be obtained through the steps of:

(1) emulsifying and dispersing a thermoplastic resin at a temperature of 100° C. or higher in the presence of a solvent containing 3-alkoxy-3-methyl-1-butanol and/or 3-alkoxy-3-methyl-1-butylacetate (the alkoxy group has 1 to 5 carbon atoms and is specifically methyl, ethyl, propyl, butyl or pentyl) (specific solvent), water and a dispersion stabilizer (emulsifying and dispersing step); and (2) thereafter cooling to obtain the thermoplastic resin as particles (cooling step).

According to the above production method, spherical thermoplastic resin particles having small particle diameter, narrow particle size distribution and excellent optical properties may be produced by using a highly safe alcohol solvent without using skin irritating organic solvents (such as xylene, toluene, n-methylpyrrolidone, chloroform, methylene chloride, dioxolane and THF) which are commonly used for obtaining fine particles of thermoplastic resins. 3-Alkoxy-3-methyl-1-butanol and/or 3-alkoxy-3-methyl-1-butylacetate are biodegradable and low in skin irritation, and thus adverse effects due to the residue may be reduced when the particles are used for applications such as cosmetics. Further, the production method of the present invention is useful when obtaining spherical particles of crystalline biodegradable thermoplastic resins such as polylactic acid (PLA), polybutylene succinate (PBS) and polyhydroxyalkanoate (PHA) in a wet manner. In addition, 3-alkoxy-3-methyl-1-butanol and/or 3-alkoxy-3-methyl-1-butylacetate dissolve or plasticize a thermoplastic resin at high temperatures but does not dissolve a thermoplastic resin at normal temperature, and thus the alcohol solvents may by easily recycled, which is industrially advantageous.

The generally spherical particles obtained by the production method are advantageous because the particles have superior optical properties (soft focus effect) and oil absorption property compared to particles obtained by other production methods.

(a) Emulsifying and Dispersing Step (i) Solvent

The solvent contains 3-alkoxy-3-methyl-1-butanol and/or 3-alkoxy-3-methyl-1-butylacetate (hereinafter also referred to as specific solvent). The proportion of the specific solvent in the solvent is preferably 50% by weight or more, more preferably 70% by weight or more and still more preferably 100% by weight. Examples of the solvent that may be used other than the specific solvent include lower alcohols such as methanol and ethanol, acetate ester-based solvents such as ethyl acetate and butyl acetate and the like. The specific solvent may be one that is marketed by Kuraray Co., Ltd. under the product name of Solfit. 3-Alkoxy-3-methyl-1-butanol may also be produced by the method disclosed in, for example, WO 2013/146370.

The specific solvent has an alkoxy group that has 1 to 5 carbon atoms. When the alkoxy group has more than 5 carbon atoms, the solubility thereof may be low. Examples of the alkoxy group include a methoxy group, an ethoxy group, a propoxy group, a butoxy group and a pentyloxy group. The propoxy group, the butoxy group and the pentyloxy group include not only linear groups but also all possible structural isomers. Preferably, the alkoxy group is a methoxy group, an ethoxy group or a propoxy group.

The amount of the solvent used is preferably 100 to 1200 parts by weight relative to 100 parts by weight of the thermoplastic resin. When the amount is less than 100 parts by weight, the concentration of the thermoplastic resin is too high to be sufficiently stirred and mixed in some cases. When the amount is more than 1200 parts by weight, the yield may be low compared to the size of the device. The amount may be 100 parts by weight, 200 parts by weight, 400 parts by weight, 500 parts by weight, 700 parts by weight, 800 parts by weight, 1000 parts by weight or 1200 parts by weight. The amount is more preferably 100 to 800 parts by weight and still more preferably 100 to 400 parts by weight.

(ii) Dispersion Stabilizer

The dispersion stabilizer that may be suitably used is inorganic fine particles that have undergone hydrophobic treatment. Specific examples include hydrophobic fumed silica (manufactured by Nippon Aerosil Co., Ltd.; product name AEROSIL® R972, AEROSIL® R974, AEROSIL® R976S, AEROSIL® R104, AEROSIL® R106, AEROSIL® R202, AEROSIL® R805, AEROSIL® R812, AEROSIL® R812S, AEROSIL® R816, AEROSIL® R7200, AEROSIL® R8200, AEROSIL® R9200, AEROSIL® R711, AEROSIL® RY50, AEROSIL® NY50, AEROSIL® RY200, AEROSIL® RY200S, AEROSIL® RX50, AEROSIL® NAX50, AEROSIL® RX200, AEROSIL® RX300, AEROSIL® R504), hydrophobic alumina (manufactured by Nippon Aerosil Co., Ltd.; product name AEROXIDO® Alu C), hydrophobic titanium oxide (manufactured by Nippon Aerosil Co., Ltd.; product name AEROXIDE® TiO2 T805: manufactured by Titan Kogyo, Ltd.; product name ultra fine titanium dioxide ST series, ST-455, STV-455, ST-557SA, ST-457EC, ST-457EC, ST-605EC: manufactured by Sakai Chemical Industry Co., Ltd.; product name ultra fine titanium dioxide STR series, STR-100C-LP, STR-60c-LP, STR-100W-LP, STR-100C-LF) and the like.

The dispersion stabilizer that may be used includes phosphate salts such as tricalcium phosphate (manufactured by Taihei Chemical Industrial Co., Ltd.; product name TCP-10U, etc.), magnesium phosphate, aluminum phosphate and zinc phosphate; pyrophosphate salts such as calcium pyrophosphate, magnesium pyrophosphate, aluminum pyrophosphate and zinc pyrophosphate; hydrophilic sparingly-soluble inorganic compounds such as calcium carbonate, magnesium carbonate, calcium hydroxide, magnesium hydroxide, aluminum hydroxide, calcium metasilicate, calcium sulfate, barium sulfate and colloidal silica (manufactured by Nissan Chemical Corporation: product name Snowtex series, Snowtex 40, Snowtex S, Snowtex XS, etc.); and the like.

Among others, tricalcium phosphate and colloidal silica are particularly preferred because desired resin particles can be stably obtained.

The amount of the dispersion stabilizer added to the thermoplastic resin is preferably 0.5 to 15% by weight. The amount may be 0.5% by weight, 0.7% by weight, 1.0% by weight, 1.2% by weight, 1.5% by weight, 3% by weight, 5% by weight, 8% by weight, 10% by weight or 15% by weight.

According to the method of the present invention, a surfactant such as an anionic surfactant, a cationic surfactant, a zwitterionic surfactant and a nonionic surfactant may be used in combination with the dispersion stabilizer.

Examples of the anionic surfactant include fatty acid oils such as sodium oleate and castor oil potassium salt; salts of alkyl sulfate esters such as sodium lauryl sulfate, ammonium lauryl sulfate; alkyl benzene sulfonates such as sodium dodecylbenzene sulfonate; alkyl naphthalene sulfonates, alkane sulfonates, dialkyl sulfosuccinates, salts of alkyl phosphate esters, naphthalenesulfonic acid-formaldehyde condensates, salts of polyoxyethylene alkyl phenyl ether sulfates, salts of polyoxyethylene alkyl sulfate esters and the like. Examples of the nonionic surfactant include polyoxyethylene alkyl ethers, polyoxyethylene alkyl phenyl ethers, polyoxyethylene fatty acid esters, sorbitan fatty acid esters, polyoxysorbitan fatty acid esters, polyoxyethylene alkyl amines, glycerol fatty acid esters, oxyethylene-oxypropylene block polymers and the like. Examples of the cationic surfactant include alkyl amine salts such as laurylamine acetate and stearylamine acetate; and quaternary ammonium salts such as lauryl trimethyl ammonium chloride. Examples of the zwitterionic surfactant include lauryldimethylamine oxide and the like.

The amount of the surfactant added is preferably 0.01 to 0.5% by weight relative to water.

The dispersion stabilizer and the surfactant are used by appropriately adjusting the types, combinations, amounts and the like thereof by taking into account the particle diameter and dispersion stability of the obtained resin particles.

(iii) Amount of Water Used

The amount of water used is preferably 100 tp 2200 parts by weight relative to 100 parts by weight of the thermoplastic resin. When the amount is less than 100 parts by weight, the concentration of the thermoplastic resin is too high to be sufficiently stirred and mixed in some cases. When the amount is more than 2200 parts by weight, the yield may be low compared to the size of the device. The amount of water used may be 100 parts by weight, 150 parts by weight, 200 parts by weight, 300 parts by weight, 600 parts by weight, 800 parts by weight, 1000 parts by weight, 1500 parts by weight, 2000 parts by weight or 2200 parts by weight. The amount is more preferably 150 to 1000 parts by weight and still more preferably 200 to 800 parts by weight.

(iv) Heat Stirring

Heat stirring is carried out under a heating temperature of 100° C. or higher. When the heating temperature is less than 100° C., the thermoplastic resin may not soften and thus fine particles may not be formed. Heat stirring may be carried out at a temperature of 180° C. or lower. The heating temperature may be 100° C., 120° C., 140° C., 160° C. or 180° C.

The generally spherical particles obtained by the present production method have a narrow particle diameter distribution. This is because the emulsion obtained at the stage of emulsion formation is extremely uniform. Therefore, in order to obtain sufficient shear force for formation of the emulsion, stirring according to known methods is sufficient, and mixing may be carried out by generally known methods such as liquid phase stirring with stirring blades, mixing with a homogenizer and ultrasonication.

The speed and time of stirring are not particularly limited as far as the thermoplastic resin may be dissolved or uniformly dispersed in a solvent, and may be appropriately selected.

Heat stirring is generally carried out in atmospheric pressure, and may be carried out under reduced or increased pressure as needed.

(b) Cooling Step

In order to deposit the thermoplastic resin as particles, the solvent containing the thermoplastic resin is cooled after heat stirring. The cooling temperature is generally normal temperature (about 25° C.). It is preferable that the time required to reach the cooling temperature from the temperature of heat stirring is as short as possible. Cooling is also preferably carried out while stirring. The stirring speed may be in a similar range as the stirring speed during heat stirring.

The generally spherical particles in the solvent after cooling may be recovered from the solvent by filtration, dehydration and drying as needed. Filtration, dehydration and drying are not particularly limited and may be carried out according to well-known methods.

EXAMPLES

The present invention is hereinafter more specifically described by way of Examples which do not limit the present invention. The measurement methods and evaluation methods used in Examples and Comparative Examples are first explained.

(Measurement of Sphericity)

The sphericity is measured with a flow particle image analyzer (product name "FPIA®-3000S", manufacture by Sysmex Corporation).

Specifically, a surfactant aqueous solution is obtained by adding to 20 mL of ion-exchange water 0.05 g of surfactant, preferably an alkylbenzene sulfonate, as a dispersant. Thereafter, 0.2 g of resin particles to be measured is added to the surfactant aqueous solution, the solution is ultrasonicated for 5 minutes on an ultrasonic dispersing device, "BRANSON SONIFIER 450" (output: 400 W, frequency: 20 kHz) manufactured by Branson Ultrasonics to disperse the resin particles in the surfactant aqueous solution, thereby obtaining a dispersion for measurement.

The above flow particle image analyzer containing a regular objective lens (10-fold) is used for measurements, and a sheath fluid used for the flow particle image analyzer is particle sheath (product name "PSE-900A", manufactured by Sysmex Corporation). The dispersion for measurement prepared according to the above procedure is introduced into the flow particle image analyzer and subjected to measurement under the following conditions:

Measurement mode: HPF measurement mode

Measuring range of particle diameter: 2.954 μm to 30.45 μm

Measuring range of particle sphericity: 0.5 to 1.0

The number of particles measured: 1000

Before the measurement, a suspension of standard polymer particles (such as "5200A" (standard polystyrene particles diluted in ion-exchange water) manufactured by Thermo Fisher Scientific) is used to perform automatic focusing of the flow particle image analyzer. The sphericity is a value obtained by dividing the boundary length calculated from the diameter of the true circle having the same projected area as the image of a resin particle by the boundary length of the image of the resin particle.

(Measurement of Volume Average Particle Diameter and Coefficient of Variance (CV))

Coulter Counter Method

The volume average particle diameter of resin particles are measured on a Coulter Multisizer™3 (analyzer manufactured by Beckman Coulter, Inc.). The measurement is performed with an aperture calibrated according to the Multisizer™3 user's manual published by Beckman Coulter, Inc.

The aperture used for the measurement is appropriately selected according to the size of resin particles measured. When it is assumed that the volume average particle diameter of resin particles is 1 μm or more and 10 μm or less, an aperture having a size of 50 μm is selected, when it is assumed that the volume average particle diameter of resin particles measured is more than 10 μm and 30 μm or less, an aperture having a size of 100 μm is selected, when it is assumed that the volume average particle diameter of resin particles measured is more than 30 μm and 90 μm or less, an aperture having a size of 280 μm is selected, when it is assumed that the volume average particle diameter of resin particles is more than 90 μm and 150 μm or less, an aperture having a size of 400 μm is selected, and so on. When the measured volume average particle diameter is different from the assumed volume average particle diameter, a measurement is performed again with an aperture having an appropriate size.

Current (aperture current) and Gain are appropriately set according to the size of the aperture selected. When an aperture having a size of 50 μm is selected, Current (aperture current) is set at −800 and Gain is set at 4, when an aperture having a size of 100 μm is selected, Current (aperture current) is set at −1600 and Gain is set at 2, and when apertures having sizes of 280 μm and 400 μm are selected, Current (aperture current) is set at −3200 and Gain is set at 1.

The measurement sample used is a dispersion obtained by dispersing 0.1 g of resin particles in 10 mL of 0.1% by weight nonionic surfactant aqueous solution by using a touch mixer (manufactured by Yamato Scientific Co., Ltd., "TOUCHMIXER MT-31") and a ultrasonic cleaner (manufactured by Velvo-Clear, "ULTRASONIC CLEANER VS-150"). The sample in a beaker is mildly stirred without generating bubbles during the measurement and the measurement is finished when 100,000 resin particles are counted. The volume average particle diameter of resin particles is an arithmetic average in the volume-based particle size distribution of 100,000 resin particles.

The coefficient of variance (CV) of the particle diameter of resin particles is calculated according to the following mathematical formula:

Coefficient of variance of the particle diameter of resin particles=(Standard deviation of the volume-based particle size distribution of the resin particles/Volume average particle diameter of resin particles)×100

(Measurement of Linseed Oil Absorption)

The linseed oil absorption of resin particles is measured by a method modified from the measurement method in JIS K 5101-13-2-2004, in which purified linseed oil is used instead of boiled linseed oil and the decision of the end point is modified (so that the end point is at which "paste (resin particles mixed and kneaded with purified linseed oil) starts flowing when the measurement plate is in an upright position"). The detailed measurement of the linseed oil absorption is as follows.

(A) Device and tools

Measurement plate: a smooth glass plate bigger than 300×400×5 mm

Pallet knife (spatula): one made of steel or stainless steel and with a blade and a haft Chemical scale (weighing machine): one allows measurements up to the order of 10 mg Burette: one defined in JIS R 3505:1994 with a capacity of 10 mL (B) Reagent Purified linseed oil: one defined in ISO 150:1980 (in the present Examples, linseed oil, first grade (manufactured by Wako Pure Chemical Industries Ltd.) is used)

(C) Measurement method (1) Resin particles (1 g) are placed on the center of the measurement plate, purified linseed oil is gradually added to the center of the resin particles with 4 to 5 drops at a time from the burette, and the resin particles and purified linseed oil are thoroughly kneaded with the palette knife after each dropwise addition.

(2) After repeating the dropwise addition and kneading and when the resin particles and purified linseed oil form a putty-like solid mass, purified linseed oil is added dropwise with a drop at a time, and the point at which paste (resin particles mixed and kneaded with purified linseed oil) becomes suddenly soft and starts flowing after addition of a drop of purified linseed oil is regarded as the end point.

(3) Judgement of flowing

When paste becomes suddenly soft and moves with the measurement plate in the upright position after addition of a drop of purified linseed oil, it is judged that the paste is flowing. When paste does not move when the measurement plate is in the upright position, another drop of purified linseed oil is added.

(4) The amount of purified linseed oil consumed at the end point is read, which is the amount of the liquid decreased in the burette.

(5) One measurement is performed so that the measurement finishes within 7 to 15 minutes. When the measurement takes longer than 15 minutes, another measurement is performed and the value taken as a result is one obtained by the measurement completed within the defined time.

(D) Calculation of linseed oil absorption

The linseed oil absorption per 100 g of sample is calculated according to the following equation:

$$O=(V/m)\times 100$$

wherein O: linseed oil absorption (mL/100 g), m: the weight (g) of resin particles, V: volume (mL) of consumed purified linseed oil.

(Measurement of Light Scattering Index)

(i) Measurement of reflected luminance distribution

According to the following method, the diffusion of light reflected at the surface of resin particles is evaluated.

The reflected luminance distribution of resin particles is measured with a three-dimensional photometer (goniophotometer GP-200 manufactured by Murakami Color Research Laboratory Co., Ltd.) in an environment of room temperature 20° C. and relative humidity of 65%.

Specifically, (1) as illustrated in FIG. 1, a double-sided adhesive tape (ORT-1 manufactured by Nitto Denko Corporation) 3 which is cut into a square of 2 cm on a side is adhered to the center of a black ABS resin plate (manufactured by Takiron Co., Ltd.) 4 having a thickness of 2 mm.

(2) Next, resin particles 2 are dropped onto the adhesive surface of the double-sided tape 3 on the black part of the black ABS resin plate 4 by using a funnel and a funnel stage (JIS K5101-12-1-2004) of an apparent density analyzer, and excess resin particles on the adhesive surface are blown away with compressed air of 0.05 to 0.1 MPa.

(3) The black ABS resin plate 4 is mounted on a flat glass plate, another 5-cm-square flat glass plate weighing 250 g is mounted on the point deposition surface of resin particles 2 and load is applied on the resin particles 2 and left as it is for 1 minute. Thereafter, excess resin particles on the adhesive surface are again blown away with compressed air.

(4) The specimen that has undergone the procedures of (2) and (3) repeated three times is obtained as specimen 1 for measurement of reflected luminance distribution. Reflected light from the obtained specimen 1 is then measured as follows. As illustrated in FIG. 1, light 5 from the light source of a halogen lamp is allowed to enter the specimen 1 (resin particles 2) at an angle of −45° relative to the normal line (0°) of the specimen 1 (resin particles 2), and the luminance distribution of reflected light 6 in the reflection angle range of −90° to +90° is measured with the three-dimensional photometer. The position of the specimen 1 is adjusted so that all incident light enters the black part of the specimen 1. Reflected light is detected with a photomultiplier having a spectral sensitivity of 185 to 850 nm and a maximum sensitivity wavelength of 530 nm.

(ii) Calculation of 0° reflected light intensity relative to +45° reflected light intensity which is regarded as 100

From the reflected light intensity data (peak luminance data) at reflection angles of 0° and +45° obtained during measurements of the reflected luminance distribution, the reflected light intensity (peak luminance) at a reflection angle of 0° relative to the reflected light intensity (peak luminance) at a reflection angle of +45° which is regarded as 100 is determined. When the reflected light intensity at a reflection angle of 0° relative to the reflected light intensity at a reflection angle of +45° (regular reflection) which is regarded as 100 approaches 100, the soft focus effect when the particles are added to cosmetics increases. The light scattering index is calculated according to the following equation:

Light scattering index=(Scattered light intensity at 0°)/(Scattered light intensity at 45°)

When the value is close to 1, it can be said that the particles show high light scattering properties independent to the angle.

Example 1

To a 300-mL autoclave, 20 g of thermoplastic resin, polybutylene succinate (manufactured by Mitsubishi Chemical Corporation, GS-Pla®, product number: FZ71PD), 60 g of solvent, 3-methoxy-3-methyl-1-butanol (manufactured by Kuraray Co., Ltd., Solfit Fine Grade), 100 g of ion-exchange water, 20 g of dispersant, 10% tricalcium phosphate aqueous solution (manufactured by Taihei Chemical Industrial Co., Ltd., TCP-10U), and 0.24 g of surfactant, sodium lauryl sulfate were added, and stirred at a reaction temperature (heat stirring temperature) of 120° C. and a stirring rotation speed of 400 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 2

To a 300-mL autoclave, a mixed solution containing 20 g of thermoplastic resin, polybutylene succinate (manufactured by Mitsubishi Chemical Corporation, GS-Pla®, product number: FZ71PD), 60 g of solvent, 3-methoxy-3-methyl-1-butanol (manufactured by Kuraray Co., Ltd., Solfit Fine Grade), 120 g of ion-exchange water and 1.5 g of dispersant, hydrophobic fumed silica (manufactured by Nippon Aerosil Co., Ltd., AEROSIL® R972) dispersed therein was added. After the addition, the mixed solution was stirred at a reaction temperature of 120° C. and a stirring rotation speed of 400 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 3

To a 300-mL autoclave, a mixed solution containing 40 g of thermoplastic resin, polybutylene succinate (manufactured by Mitsubishi Chemical Corporation, GS-Pla®, product number: FZ71PD), 60 g of solvnet, 3-methoxy-3-methyl-1-butanol (manufactured by Kuraray Co., Ltd., Solfit Fine Grade), 100 g of ion-exchange water and 3 g of dispersant, hydrophobic fumed silica (manufactured by Nippon Aerosil Co., Ltd., AEROSIL® R972) dispersed therein was added. After the addition, the mixed solution was stirred at a reaction temperature of 120° C. and a stirring rotation speed of 400 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 4

To a 300-mL autoclave, a mixed solution containing 20 g of thermoplastic resin, polybutylene succinate (manufactured by Mitsubishi Chemical Corporation, GS-Play', product number: FZ71PD), 60 g of solvent, 3-methoxy-3-methyl-1-butanol (manufactured by Kuraray Co., Ltd., Solfit Fine Grade), 120 g of ion-exchange water, 0.12 g of surfactant, polyoxyethylene styrenated phenyl ether (manufactured by DKS Co., Ltd., product name; Neugen EA-167) and 1.5 g of dispersant, hydrophobic fumed silica (manufactured by Nippon Aerosil Co., Ltd., AEROSIL® R972) dispersed therein was added. After the addition, the mixed solution was stirred at a reaction temperature of 120° C. and a stirring rotation speed of 400 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 5

To a 1500-mL autoclave, a mixed solution containing 120 g of thermoplastic resin, polybutylene succinate (manufactured by Mitsubishi Chemical Corporation, GS-Pla®, product number: FZ71PD), 360 g of solvent, 3-methoxy-3-methyl-1-butanol (manufactured by Kuraray Co., Ltd., Solfit Fine Grade), 720 g of ion-exchange water and 6 g of dispersant, hydrophobic fumed silica (manufactured by Nippon Aerosil Co., Ltd., AEROSIL® R972) dispersed therein was added. After the addition, the mixed solution was stirred at a reaction temperature of 120° C. and a stirring rotation speed of 400 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 6

To a 1500-mL autoclave, a mixed solution containing 240 g of thermoplastic resin, polybutylene succinate (manufactured by Mitsubishi Chemical Corporation, GS-Pla®, product number: FZ71PD), 420 g of solvent, 3-methoxy-3-methyl-1-butanol (manufactured by Kuraray Co., Ltd., Solfit Fine Grade), 540 g of ion-exchange water and 18 g of dispersant, hydrophobic silica (manufactured by Nippon Aerosil Co., Ltd. AEROSIL® R972) dispersed therein was added. After the addition, the mixed solution was stirred at a reaction temperature of 120° C. and a stirring rotation speed of 600 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 7

To a 1500-mL autoclave, a mixed solution containing 240 g of thermoplastic resin, polybutylene succinate (manufactured by Mitsubishi Chemical Corporation, GS-Pla®, product number: FZ91PD), 480 g of solvent, 3-methoxy-3-methyl-1-butanol (manufactured by Kuraray Co., Ltd., Solfit Fine Grade), 480 g of ion-exchange water and 18 g of dispersant, hydrophobic fumed silica (manufactured by Nippon Aerosil Co., Ltd., AEROSIL® R972) dispersed therein was added. After the addition, the mixed solution was stirred at a reaction temperature of 120° C. and a stirring rotation speed of 600 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 8

To a 1500-mL autoclave, a mixed solution containing 240 g of thermoplastic resin, polybutylene succinate (manufactured by Mitsubishi Chemical Corporation, GS-Pla®, product number: FZ71PD), 480 g of solvent, 3-methoxy-3-methyl-1-butanol (manufactured by Kuraray Co., Ltd., Solfit Fine Grade), 480 g of ion-exchange water and 12 g of dispersant, hydrophobic fumed silica (manufactured by Nippon Aerosil Co., Ltd., AEROSIL® R976S) dispersed therein was added. After the addition, the mixed solution was stirred at a reaction temperature of 120° C. and a stirring rotation speed of 600 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 9

To a 1500-mL autoclave, 240 g of thermoplastic resin, polybutylene succinate (manufactured by Mitsubishi Chemical Corporation, GS-Pla®, product number: FZ71PD), 480 g of solvent, 3-methoxy-3-methyl-1-butanol (manufactured by Kuraray Co., Ltd., Solfit Fine Grade), 240 g of ion-exchange water, 240 g of dispersant, 10% tricalcium phosphate aqueous solution (manufactured by Taihei Chemical Industrial Co., Ltd., TCP-10U), and 0.48 g of surfactant, sodium lauryl sulfate were added, and stirred at a reaction temperature (heat stirring temperature) of 120° C. and a stirring rotation speed of 600 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 10

To a 1500-mL autoclave, a mixed solution containing 240 g of thermoplastic resin, polylactic acid (manufactured by Unitika Ltd., Terramac®, product number: TE-2500), 480 g of solvent, 3-methoxy-3-methyl-1-butanol (manufactured by Kuraray Co., Ltd., Solfit Fine Grade), 480 g of ion-exchange water and 18 g of dispersant, hydrophobic fumed silica (manufactured by Nippon Aerosil Co., Ltd., AEROSIL® R972) dispersed therein was added. After the addition, the mixed solution was stirred at a reaction temperature of 140° C. and a stirring rotation speed of 600 rpm for 90 minutes Thereafter, while maintaining the stirring rotation speed, the autoclave was rapidly cooled (in 30 minutes to 25° C.) and the content was removed. The content was subjected to dehydration, filtration and drying to obtain generally spherical particles.

Example 11

To a 1500-mL autoclave, a mixed solution containing 240 g of thermoplastic resin, 3-hydroxybutyrate/3-hydroxyhexanoate copolymer (manufactured by Kaneka Corporation, Kaneka biopolymer Aonilex®, product number: X131A), 480 g of solvent, 3-methoxy-3-methyl butanol (manufactured by Kuraray Co., Ltd., Solfit Fine Grade), 480 g of ion-exchange water and 24 g of dispersant, hydrophobic fumed silica (manufactured by Nippon Aerosil Co., Ltd., AEROSIL® 974) dispersed therein was added. After the addition, the mixed solution was stirred at a reaction temperature of 130° C. and a stirring rotation speed of 600 rpm for 90 minutes.

Thereafter, while maintaining the stirring rotation speed, the autoclave was rapidly cooled (in 30 minutes to 25° C.) and the content was removed. The content was subjected to dehydration, filtration and drying to obtain generally spherical particles.

Comparative Example 1

Ganzperal GMX-0810 manufactured by Aica Kogyo Co., Ltd. was used for various measurements.

Comparative Example 2

To a 300-mL autoclave, a mixed solution containing 20 g of thermoplastic resin, polybutylene succinate (manufactured by Mitsubishi Chemical Corporation, GS-Pla®, product number: FZ71PD), 60 g of solvent, 3-methoxy-3-methyl-1-butanol (manufactured by Kuraray Co., Ltd., Solfit Fine Grade), 120 g of ion-exchange water, 1.5 g of dispersant, hydrophobic fumed silica (manufactured by Nippon Aerosil Co., Ltd., AEROSIL® R972) dispersed therein was added. After the addition, the mixed solution was stirred at a reaction temperature of 90° C. and a stirring rotation speed of 400 rpm for 90 minutes.

Thereafter, while maintaining the stirring rotation speed, the autoclave was rapidly cooled (in 30 minutes to 25° C.) and the content was removed. However, the content was still in the form of pellets and thus fine particles could not be obtained.

Various properties of the generally spherical particles obtained in Examples are indicated in the following Table.

TABLE 1

| | Heat stirring temperature | Sphericity | Average particle diameter | CV | Linseed oil absorption | Scattered light intensity | | Light scattering index |
| --- | --- | --- | --- | --- | --- | --- | --- | --- |
| | ° C. | | μm | | mL/100 g | 0° | 45° | |
| Example 1 | 120 | 0.98 | 20 | 57.2 | 125 | 84.72 | 95.13 | 0.89 |
| Example 2 | 120 | 0.933 | 22 | 52.9 | 108 | 82.19 | 99.59 | 0.825 |
| Example 3 | 120 | 0.985 | 19 | 40.4 | 90 | 86.6 | 99.97 | 0.866 |
| Example 4 | 120 | 0.985 | 19 | 52.2 | 97 | 74.94 | 100.87 | 0.742 |
| Example 5 | 120 | 0.95 | 14 | 57.9 | 108 | 62 | 87 | 0.71 |
| Example 6 | 120 | 0.976 | 12 | 49.8 | 114 | 51.58 | 98.79 | 0.522 |
| Example 7 | 120 | 0.971 | 15 | 44.5 | 117 | 82.99 | 99.86 | 0.831 |
| Example 8 | 120 | 0.964 | 19 | 39.1 | 99 | 87.05 | 99.57 | 0.874 |
| Example 9 | 120 | 0.972 | 20 | 41.4 | 125 | 79.47 | 99.8 | 0.796 |
| Example 10 | 140 | 0.928 | 18 | 42.2 | 142 | 84.57 | 99.66 | 0.848 |
| Example 11 | 130 | 0.957 | 19 | 50.4 | 102 | 85.49 | 89.56 | 0.954 |
| Comparative Example 1 | — | 0.97 | 12 | 38 | 70 | 31.7 | 90.34 | 0.35 |
| Comparative Example 2 | 90 | — | — | — | — | — | — | — |

It is found that the generally spherical particles obtained in Examples were obtained with specific solvents and by heat-stirring of thermoplastic resins at a temperature of 100° C. or higher followed by cooling, and thus are spherical, have small particle diameters, have narrow particle size distribution and high light scattering ability.

REFERENCE SIGNS LIST

1 Specimen, 2 Resin particles, 3 Double-sided adhesive tape, 4 Black ABS resin plate, 5 Light, 6 Reflected light

The invention claimed is:

1. Resin particles formed of a thermoplastic resin, wherein the resin particles have a sphericity of 0.90 to 1.00, a light scattering index of 0.5 to 1.0 and a linseed oil absorption of 80 to 150 mL/100 g, and wherein the thermoplastic resin is not polybutylene succinate or polyhydroxyalkanoate.

2. The resin particles formed of a thermoplastic resin according to claim 1, wherein the thermoplastic resin is at least one resin selected from the group consisting of a polyolefin-based resin, a polyester-based resin, a polyether-based resin and a polyamide-based resin.

3. The resin particles formed of a thermoplastic resin according to claim 1, wherein the thermoplastic resin is at least one resin selected from the group consisting of polyethylene, polypropylene, an ethylene/vinyl acetate copolymer, an ethylene/(meth)acrylic acid copolymer, an ethylene/(meth)acrylate ester copolymer, polylactic acid, polycaprolactam, Nylon 12 and Nylon 6.

4. The resin particles formed of a thermoplastic resin according to claim 1, wherein the thermoplastic resin is biodegradable and is at least one resin selected from the group consisting of a polyester-based resin and a polyether-based resin.

5. The resin particles formed of a thermoplastic resin according to claim 1, wherein the thermoplastic resin is dissolved or plasticized in 3-alkoxy-3-methyl-1-butanol and/or 3-alkoxy-3-methyl-1-butylacetate (the alkoxy group has 1 to 5 carbon atoms) at 100° C. or higher and is not dissolved therein at normal temperature.

6. A method for producing resin particles formed of a thermoplastic resin comprising emulsifying and dispersing a thermoplastic resin at a temperature of 100° C. or higher in the presence of a solvent containing 3-alkoxy-3-methyl-1-butanol and/or 3-alkoxy-3-methyl-1-butylacetate (the alkoxy group has 1 to 5 carbon atoms), water and a dispersion stabilizer followed by cooling, wherein the thermoplastic resin is not polybutylene succinate or polyhydroxyalkanoate.

7. A cosmetic comprising the resin particles formed of a thermoplastic resin according to claim 1.

8. A coating material comprising the resin particles formed of a thermoplastic resin according to claim 1.

9. The resin particles formed of a thermoplastic resin according to claim 1, wherein the resin particles are used for any application of:
 (i) compounding agents for cosmetics selected from foundations, antiperspirants and scrubes;
 (ii) various agents selected from flatting agents for paints, rheology modifying agents, antiblocking agents, lubricity imparting agent, light diffusing agents, auxiliary agents for sinter molding of fine ceramics, fillers for adhesives and medical diagnostic examination agents; and
 (iii) additives for molded articles selected from automobile materials and construction materials.

10. The resin particles formed of a thermoplastic resin according to claim 1, wherein the resin particles have a volume average particle diameter of 1 to 500 μm and a CV of 39.1 to 57.9.

11. The method for producing the resin particles formed of a thermoplastic resin according to claim 6, wherein the resin particles have a volume average particle diameter of 1 to 500 μm and a CV of 39.1 to 57.9.

\* \* \* \* \*